(12) United States Patent
Wallace et al.

(10) Patent No.: US 10,492,673 B2
(45) Date of Patent: Dec. 3, 2019

(54) VAGINAL SPECULUM

(71) Applicant: Medline Industries, Inc., Northfield, IL (US)

(72) Inventors: Corey Wallace, Brighton, MI (US); Kelley Kuehne, Williamston, MI (US)

(73) Assignee: Medline Industries, Inc., Northfield, IL (US)

( * ) Notice: Subject to any disclaimer, the term of this patent is extended or adjusted under 35 U.S.C. 154(b) by 147 days.

(21) Appl. No.: 15/612,656

(22) Filed: Jun. 2, 2017

(65) Prior Publication Data

US 2017/0347871 A1 Dec. 7, 2017

Related U.S. Application Data

(60) Provisional application No. 62/344,488, filed on Jun. 2, 2016.

(51) Int. Cl.
*A61B 1/32* (2006.01)
*A61B 1/303* (2006.01)
*A61B 1/06* (2006.01)
*A61B 1/00* (2006.01)

(52) U.S. Cl.
CPC ............ *A61B 1/303* (2013.01); *A61B 1/0669* (2013.01); *A61B 1/32* (2013.01); *A61B 1/00032* (2013.01); *A61B 1/0684* (2013.01)

(58) Field of Classification Search
CPC .................................. A61B 1/303; A61B 1/32
See application file for complete search history.

(56) References Cited

U.S. PATENT DOCUMENTS

| | | | |
|---|---|---|---|
| 3,332,414 A * | 7/1967 | Gasper | A61B 1/32 600/222 |
| 3,716,047 A | 2/1973 | Moore et al. | |
| D274,356 S | 6/1984 | Riedell | |
| 6,416,467 B1 | 7/2002 | McMillin et al. | |
| 2008/0228038 A1 | 9/2008 | McMahon et al. | |
| 2009/0069634 A1 | 3/2009 | Larkin | |
| 2012/0078060 A1 | 3/2012 | Swift | |
| 2014/0148653 A1 | 5/2014 | McMahon et al. | |

* cited by examiner

*Primary Examiner* — Christian A Sevilla
(74) *Attorney, Agent, or Firm* — Fitch, Even, Tabin & Flannery LLP

(57) ABSTRACT

A speculum includes an upper bill, a lower bill downwardly of the upper bill, a yoke moveably joining the upper bill to the lower bill, and a ratchet to hold the upper bill and lower bill at a position relative to each other, the ratchet including teeth facing upwardly to selectively hold the upper bill and lower bill. When the ratchet is moved downwardly, the upper bill may pivot freely on the yoke. When the ratchet is moved upwardly, the upper bill is fixed against pivoting. In an example, the yoke includes a pivot about which the upper bill pivots when the ratchet allows and holds the upper bill in position against pressure on the upper bill. A latch prevents the yoke from being removed from the lower bill. Guides allow the upper bill move vertically on the lower bill through the yoke.

15 Claims, 11 Drawing Sheets

VAGINAL SPECULUM

CROSS REFERENCE TO RELATED APPLICATION

The present application claims the benefit under 35 U.S.C. § 119(e) to the provisional patent application No. 62/344,488, filed 2 Jun. 2016, titled VAGINAL SPECULUM, which is hereby incorporated by reference for any purpose.

TECHNICAL FIELD

The present disclosure is generally directed to a speculum, and more specifically to a vaginal speculum that may be used to dilate the passage through the vagina for gynecological examination, treatment, sampling or the like.

BACKGROUND

A speculum operates to allow a healthcare provider the ability to visually inspect a body orifice, e.g., a vagina. A vaginal speculum may have upper and lower arms that are pivoted with respect to one another to form a set of jaws at one end and a handle on an opposite end. The handle can be squeezed by the health care provider to separate jaws. The jaws are placed into the closed state to insert into the vagina. The healthcare provider may subsequently open the jaws to cause the passageway to be sufficiently enlarged. A locking mechanism can be used to lock the pivotal position of the upper and lower arms with respect to one another. However, the locking mechanism may create a clicking sound when changing positions. The clicking sound has been found to be disturbing to patients on which a speculum is being used in a medical procedure.

SUMMARY

A speculum as described herein may include bills to be inserted into a body orifice and a ratchet and pawl that has the teeth facing upwardly to allow the pivoting of an upper bill relative to a lower bill when not engaged and holding the bills against movement when engaged.

A speculum may include an upper bill, a lower bill downwardly of the upper bill, and a yoke moveably joining the upper bill to the lower bill. A ratchet is proved to hold the upper bill and lower bill at a position relative to each other. The ratchet including teeth face upwardly to selectively hold the upper bill and lower bill.

In an embodiment, the yoke includes a pivot about which the upper bill pivots when the ratchet allows and holds the upper bill in position against pressure on the upper bill.

In an embodiment, the yoke allows vertical movement of the upper bill relative to the lower bill.

In an embodiment, the yoke includes a toggle to hold the yoke relative to the lower bill which in turn holds the upper bill vertically.

In an embodiment, the upper bill includes an aperture through which the ratchet extends and a pawl that defines an upper edge of the aperture.

In an embodiment, the ratchet is pivotally connected to the yoke to allow the ratchet to move vertically upwardly into engagement with the pawl and move downwardly out of engagement with the pawl.

In an embodiment, the yoke includes a pivot axis at a top thereof at which the upper bill pivots on the yoke.

In an embodiment, the lower bill includes a first latch and the yoke includes a second latch that engages the first latch to prevent the yoke from being released from the lower bill.

In an embodiment, the yoke includes arms above a base with the arms engaging an upper part of the lower bill to guide the yoke relative to the lower bill.

In an embodiment, the yoke includes a recess in each of the arms and a guide on both sides of the lower bill to engage in the recesses.

A speculum may include an upper bill assembly, a lower bill assembly, a yoke moveably joining the upper bill to the lower bill to allow the upper bill assembly to pivot and to allow the upper bill assembly and the lower bill assembly to move vertically relative to each other, and a ratchet means for releasing the upper bill and the lower bill for relative movement such that teeth are completely free for movement in a first position and moveable to engaged position for holding the upper bill from pivoting relative to the lower bill.

In an embodiment, the yoke includes a pivot about which the upper bill assembly pivots when the ratchet allows and holds the upper bill assembly in position against pressure on the upper bill assembly.

In an embodiment, the yoke allows vertical movement of the upper bill assembly relative to the lower bill assembly.

In an embodiment, the yoke includes a toggle to hold the yoke relative to the lower bill assembly which in turn holds the upper bill assembly.

In an embodiment, the yoke includes a pivot axis at a top thereof at which the upper bill pivots on the yoke.

In any of these embodiments, the speculum may be a vaginal speculum.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention. Also, as used herein the term "proximal" refers to the direction generally towards the health care provider during a procedure, while the term "distal" refers to the direction generally away from the health care provider during a procedure.

The present disclosure describes embodiments of a speculum for use in medical procedures that reduces the click sound when the speculum is moved or ratcheted to an open position. The present speculum may not produce a "click" when opening or between incremental steps when opening and holding the speculum in the selected incremental open position. In an example embodiment, the speculum includes a curved, toothed arm that engages the upper arm through and aperture therein, which can selectively hold the speculum in the open position. When the speculum moves between the selectable open position, the arm and teeth reduce the amount of clicking noise.

Figure 1:
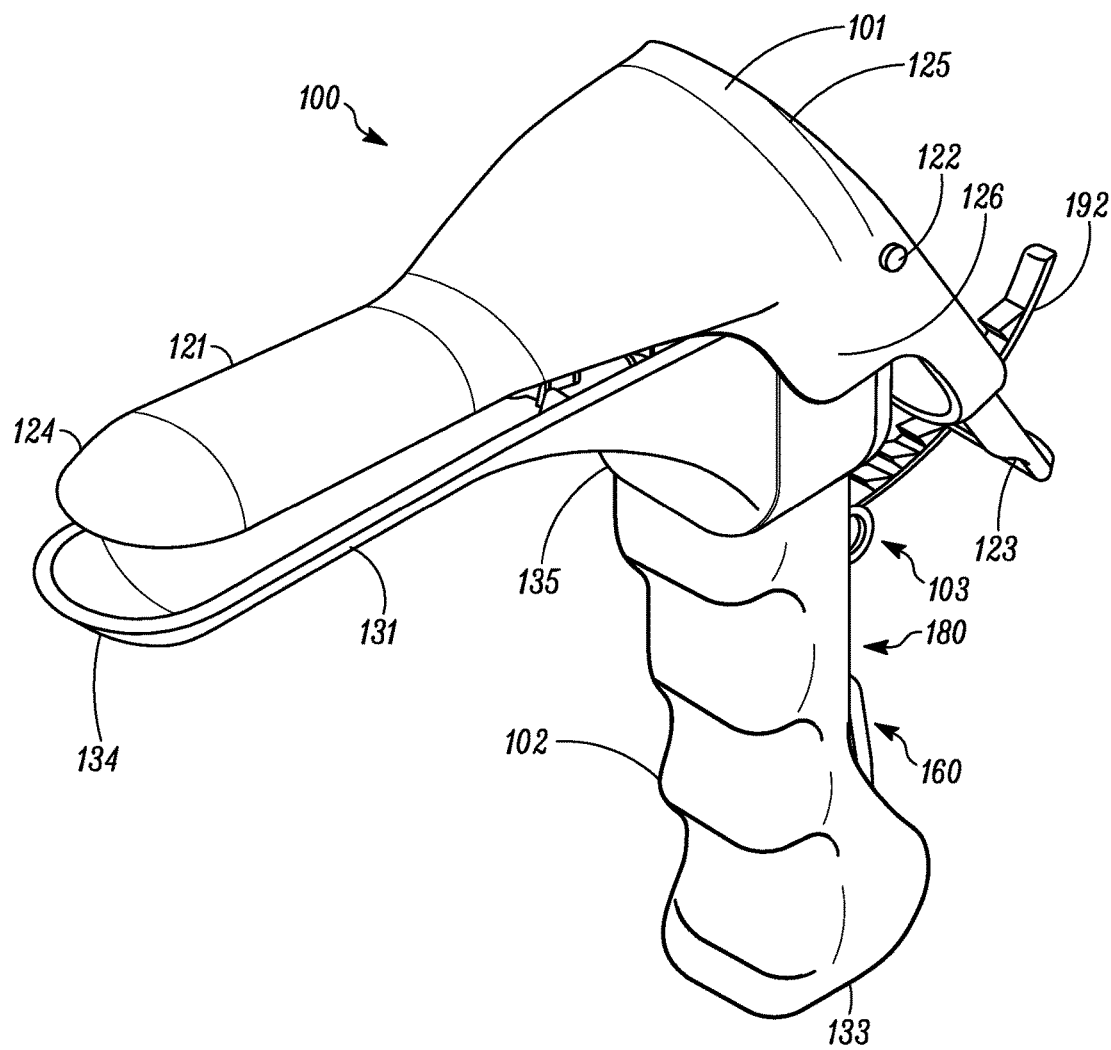
FIG. 1 is a perspective view of a speculum according to an example embodiment.
Figure 3:
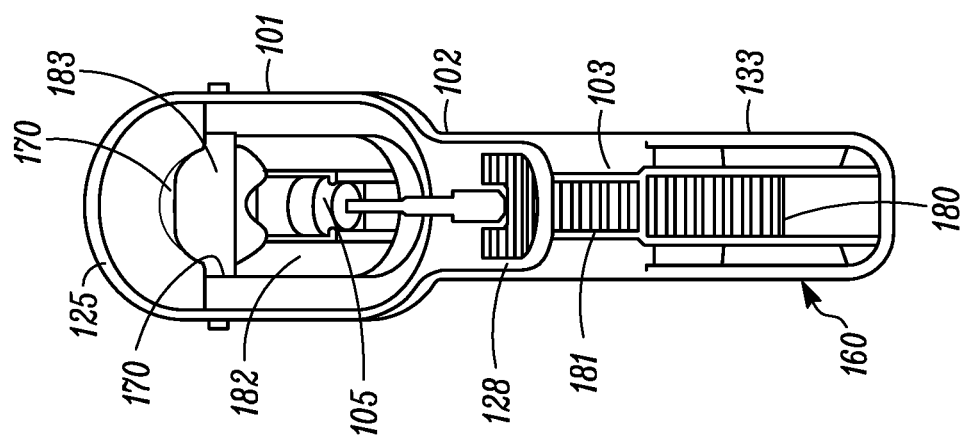
FIG. 3 is a rear view of a speculum according to an example embodiment.

FIG. 1 shows a perspective view of a speculum 100 that includes an upper bill assembly 101, a lower bill assembly 102 and a yoke 103 movably joining the upper bill assembly 101 to the lower bill assembly 102. The upper bill assembly 101 and the lower bill assembly 102 are adapted to move from a closed, insertion position to an open position to open a bodily orifice for inspection by a healthcare provider. In an example, the speculum 100 may be adapted for insertion into a vagina for gynecological examination, treatment, and/or sampling. The speculum bill assemblies 101, 102 can be positioned relative to one another by the healthcare provider during and after insertion into the patient's body, e.g., from a closed position for insertion, to an open position for the medical procedure, back to a closed position for retraction. It will be appreciated that FIG. 1 shows the speculum 100 in a partially closed position. In a fully closed position, the bill assemblies 101, 102 rest on each other to form a generally cylindrical, insertable form. The front end (distal) of the bill assemblies 101, 102 may be rounded to reduce the likelihood of any corners or abrupt changes in shape to provide a smooth distal end.

In an example, the bill assemblies 101, 102 may pivot relative to each other and may slide relative to one another so that their orientation to one another can be further adjusted as desired to increase or decrease the resulting distance between the bill assemblies 101, 102. The sliding moves the bill assemblies 101, 102 apart from each other along their entire length. The pivoting action causes the distal ends of the bill assemblies 101, 102 to move apart from each other to a greater extent than at the bill part adjacent a pivot point whereat the bill assemblies pivot. The pivot point can be at the proximal end of the bill assemblies 101, 102. In some examples, the pivot point is past the proximal end. In an example, the lower bill assembly 102 is fixed in position and the upper bill assembly 101 moves relative to the lower bill assembly 102. The yoke 103 may provide structures to allow pivoting and sliding of the bill assemblies 101, 102, as well as locking the bill assemblies 101, 102 to each other. The speculum 100 may be operated by the healthcare provider using a single hand, freeing the healthcare provider's other hand for other tasks.

The upper bill assembly 101 includes an elongate bill 121 and a handle 123 proximal to the healthcare provider. The bill 121 includes a distal end 124 that narrows distally and rounded for ease of insertion into an orifice or the patient and a proximal end 125 that is larger than the distal end 124 to provide an increased viewing area for the healthcare provider. The outer surface elongate bill 121 is smooth and continuous. In an example, the entire surface of the upper bill assembly is smooth and continuous for ease of use. The distal end 124 can have a compound curve that moves into an arcuate elongate body that connects to proximal end 125, which may also have a compound curve. The arcuate shape of the bill 121 is shaped to curve upwardly. In an example, the bill 121 may be about 5.0 inches, +/−0.1 inch, +/−0.5 inch or +/−1.0 inches. The proximal end 125 also includes a flange 126 at the lower side and distal to the handle 123. The flange 126 is sized to extend on the outside of the lower bill assembly 102. The handle 123 may be integrally formed with the bill 121. The handle 123 extends downwardly from the bill 121 at the proximal end 125 while leaving the entire proximal end open for viewing through the speculum 100. The handle 123 includes an engagement structure 128 that can form part of a pivot latch mechanism, e.g., an aperture 127 with a pawl 129 to selectively receive an elongate ratchet 191. The engagement structure 128 extends downwardly and is adapted to be engaged by the healthcare provider, e.g., a finger or thumb to pivot the upper bill assembly 101 relative to the lower bill assembly. The handle 123 extends at an oblique relative to the bill 121, e.g., at angle of about 135° or 145°. In another example, the angle is in a range between 130° to 145°.

Figure 2:
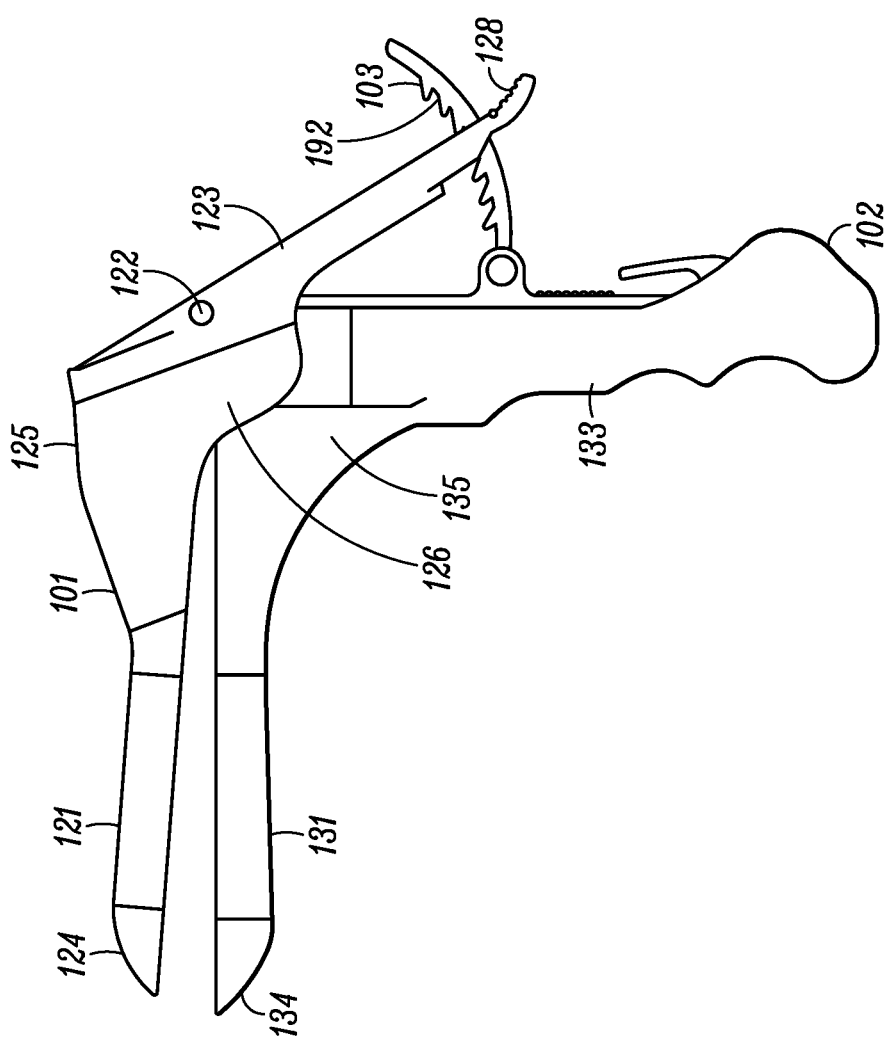
FIG. 2 is an elevational view of a speculum according to an example embodiment.
Figure 4:
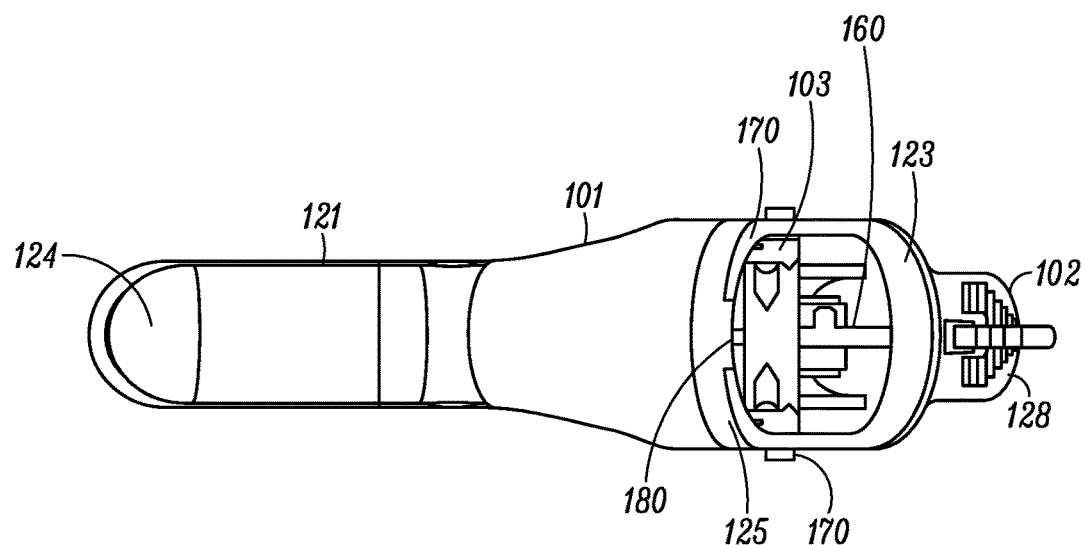
FIG. 4 is top view of a speculum according to an example embodiment.
Figure 5:
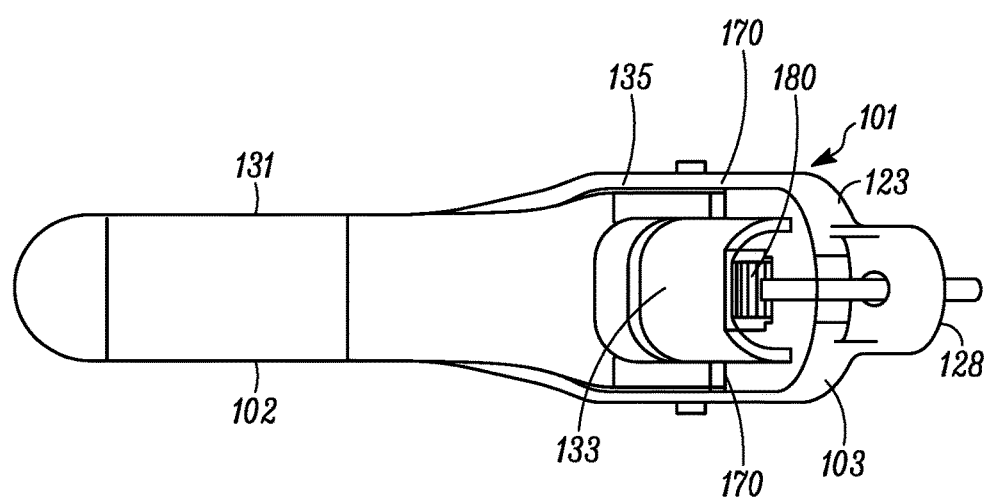
FIG. 5 is a bottom view of a speculum according to an example embodiment.
Figure 6:
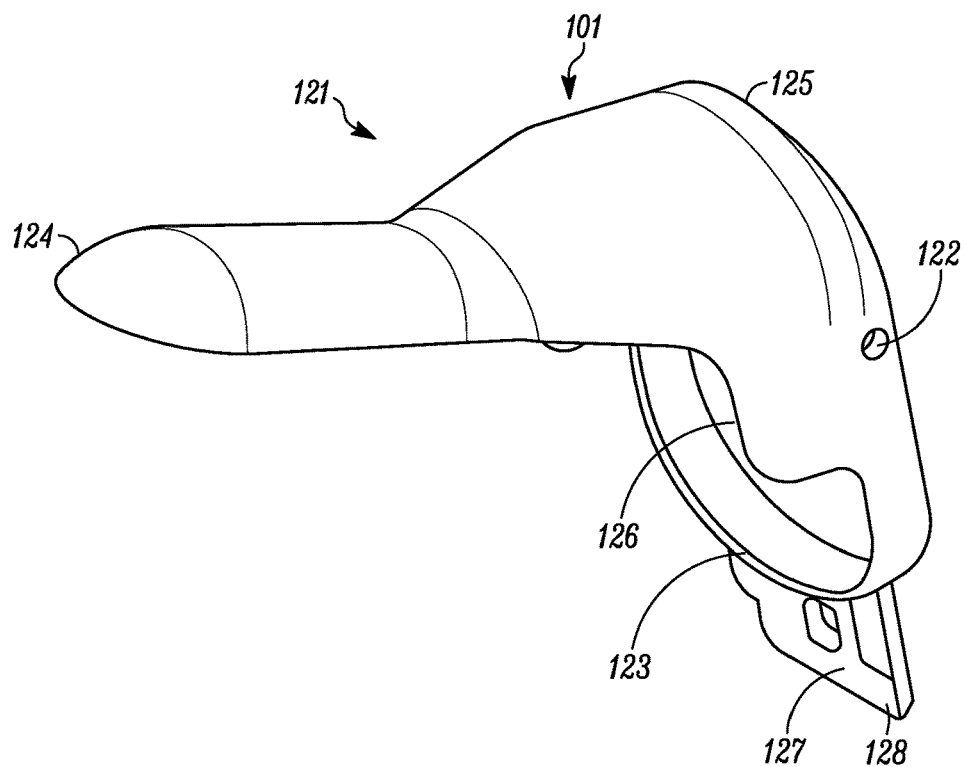
FIG. 6 is a perspective view of the top bill assembly according to an example embodiment.
Figure 7:
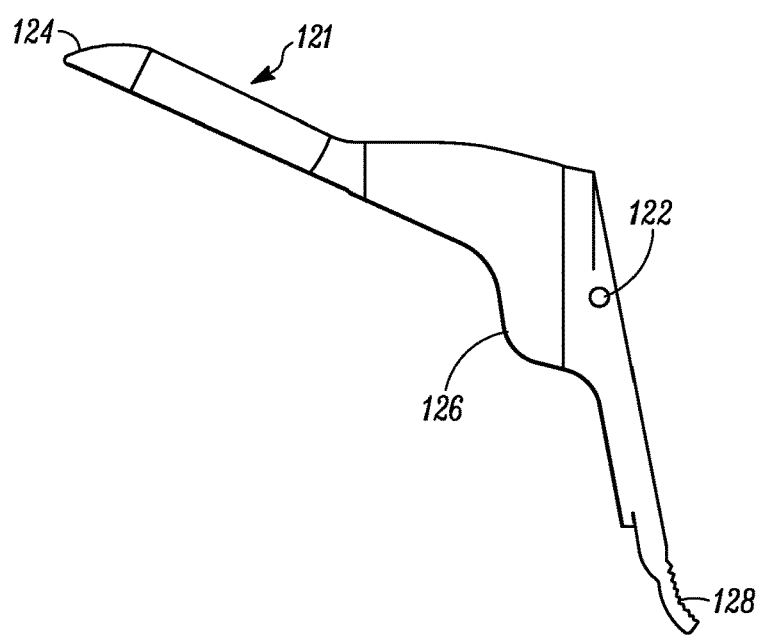
FIG. 7 is an elevation view of the top bill assembly.
Figure 8:
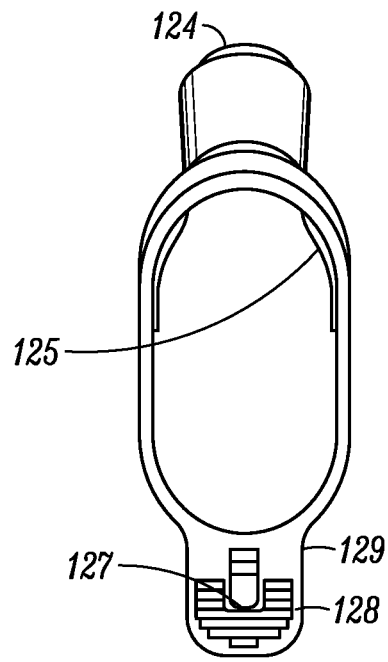
FIG. 8 is a rear view of the top bill assembly.
Figure 9:
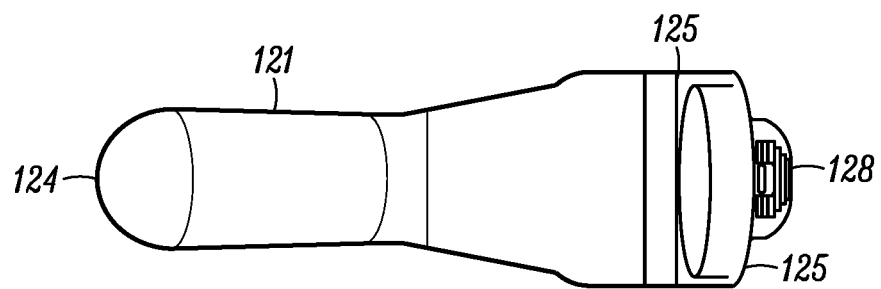
FIG. 9 is top view of the top bill assembly.

The lower bill assembly 102 includes an elongate bill 131 distal the healthcare provider and a grip 133 proximal to the healthcare provider. The bill 131 includes a distal end 134 that narrows distally and rounded for ease of insertion into a patient's orifice and a proximal end 135 that is larger than the distal end 134. The distal end 134 can have a compound curve, which transitions proximally into an arcuate elongate body that connects to proximal end 135, which may also have a polygon shape. The arcuate shape of the bill 131 is shaped to curve upwardly. In an example, the bill 131 may be about 5.0 inches, +/−0.1 inch, +/−0.5 inch or +/−1.0 inches. The proximal end 135 is shaped such that the flange 126 extends on the outside of a top part of the proximal end 135 with the speculum 100 in a closed position. (FIGS. 1 and 2). The grip 133 includes an outer wall to define an interior space, which can provide an ergonomic location for a part of a stop 150, a part of a vertical latch mechanism 160, and a guide 171 for a vertical slide mechanism 170. The stop 150 operates to keep the upper bill assembly 101 from being disengaged from the lower bill assembly 102 by a latch on the yoke 103 engaging a latch on the grip 133. The guide 171 engages the yoke 103 so that the upper bill assembly 101 smoothly moves vertically relative to the lower bill assembly 102.

The grip 133, as shown in FIGS. 1 and 2, is essentially rectangular in shape with undulations to form finger placements when held by a healthcare provider. The grip 133 extends downwardly from the bill 131, e.g., at about a right angle, +/−2°, 3°, or 5°. In an example embodiment, the grip 133 extends downwardly from a horizontally extending bill 131 at a non-right angle, but still provides a handgrip for the medical provider to manually hold the grip 133 in one hand with the bill 131 extending forwardly for insertion into the orifice of the patient.

Figure 10:
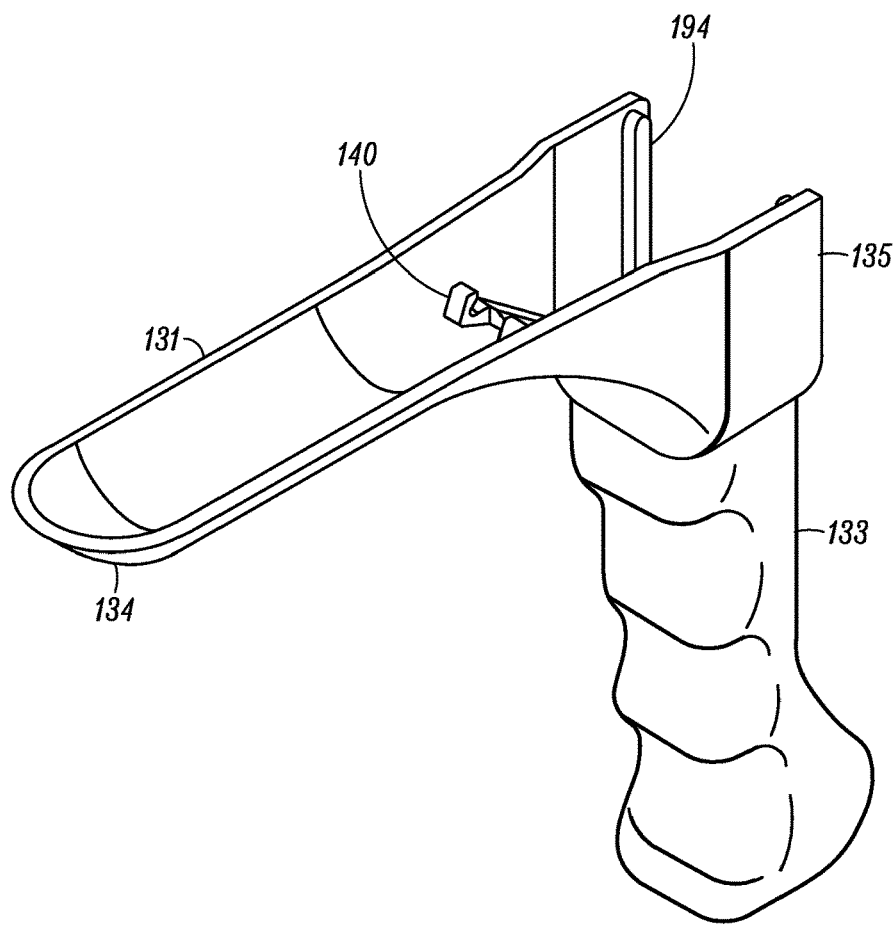
FIG. 10 is a perspective view of the bottom bill assembly.
Figure 11:
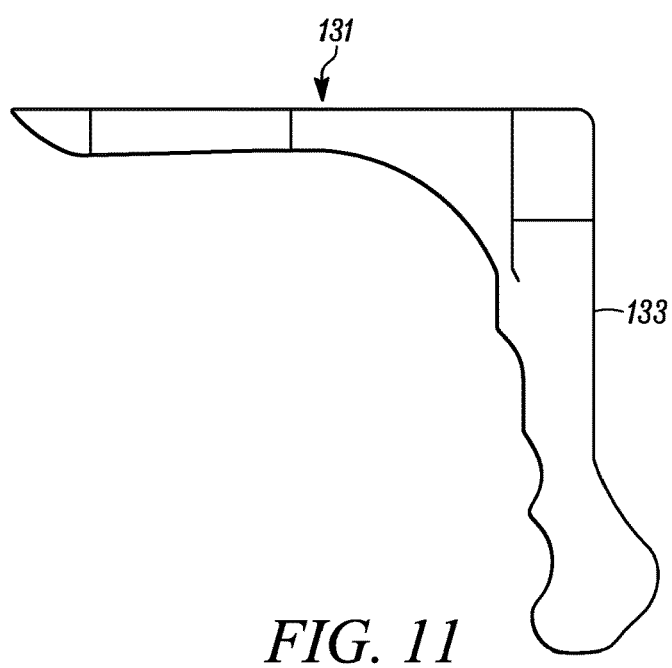
FIG. 11 is an elevation view of the bottom bill assembly.
Figure 12:
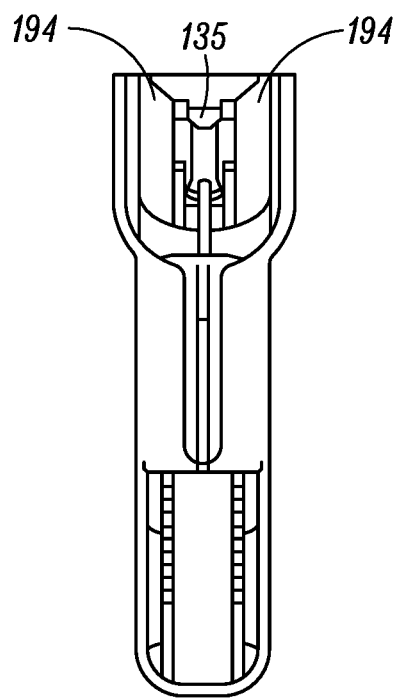
FIG. 12 is a rear view of the bottom bill assembly.
Figure 13:
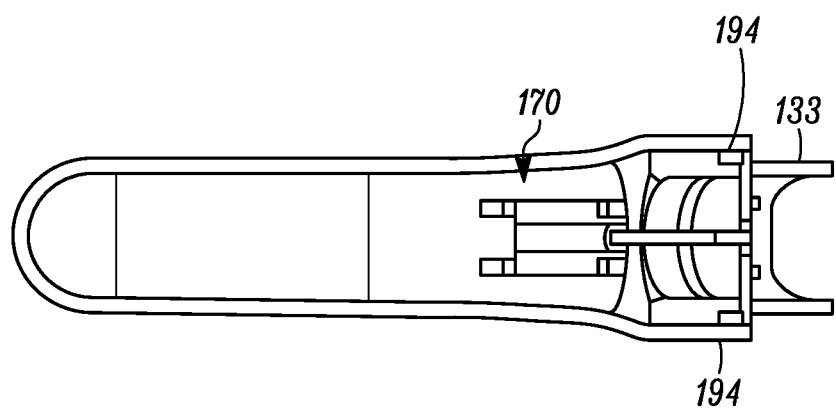
FIG. 13 is top view of the bottom bill assembly.

A light mount 140 (FIGS. 10, 12-13) is provided in the elongate bill 131. The light mount 140 is adapted to receive a light source 105. The light mount 140 can be a press fit connector, a detent connector, or other connector that can receive the light source 105. The light mount 140 secures the light source 105 in the interior of the bill 131 with the light source being directed forwardly toward the distal end of the bill 131.

The light source 105 is mounted within the speculum 100, e.g., on bill assemblies 101, 102 or along at least one of the bills 111, 112. The light source 105 selectively turned off and on by the healthcare provider. The light source is adapted to emit light along the longitudinal direction of the bills 111, 112. In an example, the light source 105 is fixed to the lower bill assembly 102. The light source 105 may include a low power light emitting diode and a power source, e.g., a plurality of batteries. The light source 105 can be a white LED. The light source 105 can emit infrared light in an example embodiment. The light source 105 can emit ultraviolet in an example embodiment. The wavelength of emission from the light source 105 can be controlled based at least in part on the type of procedure being conducted using the speculum 100. Control circuitry can be provided to light source, e.g., the LEDs that comprise the light source 105.

The light source 105 can include a lens that is mounted to a light source housing that is mounted to the receptacle in the speculum 100. The lens can be part of the bill assemblies 101 or 102, e.g., integrally molded. The bill assemblies 101 or 102 can include a light guide or pipe that optically couples to the light source 105 to receive light from the light source and to guide the light therefrom to the distal ends of the bills 121 or 131. The light source 105 can be completely housed with the speculum 100, e.g., upwardly and distally from the yoke or moveable components that join the lower bill assembly 102 to the upper bill assembly 101. In an example, the light source 105 is positioned in a proximal half of either the top bill assembly 101 or the bottom bill assembly 102.

The light source 105 can be mounted in the hollow interior of the lower bill assembly 102. A receptacle for the light source 105 can be integrally formed in one of the grip 133, the lower bill, the transition therebetween or combinations thereof. The light source 105 should be positioned to not interfere with the visual path through the speculum bills 121, 131. The grip 133 is positioned beneath the lower bill and extends essentially vertically therebeneath. The grip 133 can include a substantially cylindrical receptacle having an open end and a defined hollow interior that is sized for retaining the light source. It should be readily understood, however, that other geometries can be used. The grip 133 include an opaque section adjacent the light source 105 with the bills and other portions of the assemblies 101, 102 being transparent. In an example, the forward ends 124, 134 of the bills assemblies 101, 102 are transparent to the light emitted by the light source 105. In an example, embodiment, the entire bill 121 and 131 are transparent to the light emitted by the light source 105. The receptacle for the light source can be integrally formed in the lower bill assembly 102.

The yoke 103 (see, FIGS. 1-5 and 14-16) includes a base 181 and two upper arms 182, 183 extending upwardly from the top of the base 181. The upper arms 182, 183 form a U-shape. The arms 182, 183 can be cantilevered from the top of the base 181. The base 181 is elongate and wider than the two arms 182, 183. The base 181 at the bottom end supports a first latch 185 that includes a web 186 extending rearwardly from the base 181 on which is placed a toggle 187 that is urged into engagement with a track of ridges on the rear face of the grip 133. A healthcare provider may engage one side of the toggle to release the toggle 187 from the ridge track to allow the upper bill assembly 101 to move vertically along an axis defined by the grip 133. When the toggle 187 is released, it again moves to its rest position and engages the ridge track to hold the bill assemblies 101, 102 together in place. The base 181 further includes side opening recesses 188 that engage guide walls on the grip. The recesses 188 can be open at the bottom to be assembled by sliding the yoke 103 into the guide 133. The grip guide walls may act as stops at the recesses 188 are closed at their top by the arms 182, 183.

A pivot connection 189 is positioned on the rear face of the base 181 above the latch 185 to support an elongate ratchet arm 191. The pivot connection 189 can have a receptacle that has a cylindrical aperture therein to receive a cylindrical pivot axle, which is cylindrical to match the aperture. The pivot connection 189 positions the ratchet arm 191 centrally along the center longitudinal axis of the yoke base 181. The pivot connection 189 provides a pivot axis to allow the ratchet to free pivot angularly from downwardly adjacent the base 181 to upwardly adjacent, intermediate the yoke arms 181, 182.

The ratchet arm 191 is arcuate with teeth 192 thereon. The ratchet arm 191 may have an inner radius in a range between about 1.5 inches and about 1.75 inches, +/−0.05 inches. In an example embodiment, the inner radius is between about 1.58 inches and about 1.68 inches, +/−0.08 inches. The outer radius of the arm is greater than the inner radius. The outer radius may be in a range between about 1.65 inches and about 1.8 inches, +/−0.05 inches. In an example embodiment, the outer radius is between about 1.7 inches and about 1.8 inches, +/−0.08 inches. Teeth 192 are positioned along the inner radius of the arcuate arm. A proximal end of the arm opposite the pivot connection end is free of teeth. The teeth 192 are angled back toward the pivot end of the arm. The short walls of the teeth are facing the pivot connection end of the ratchet arm 191. The apex of the teeth 192 is rounded to reduce the amount of noise when the teeth are released or engaged to change the position of the speculum.

The ratchet 191 is adapted to extend through the aperture 127 in the engagement structure 128. The aperture 127 is positioned along the central plane of the upper bill. The aperture 127 is sized large enough so that the teeth 192 of the ratchet 191 can freely move through the aperture 127 when the teeth 192 are free from the pawl 129. The ratchet 191 is held in the pivot connection 189 by a male end of the ratchet being in a receptacle in the pivot connection 189 such that the teeth 192 of the ratchet 191 extend upwardly. The ratchet 191 freely pivots at the pivot connection 189. The ratchet teeth 192 extend toward the upper bill assembly 101 when the speculum is assembled. In operation, the force applied to the upper bill or the force of the upper bill is transferred to the teeth on the ratchet to hold the upper bill from pivoting closed until the medical practitioner moves the ratchet teeth free from the pawl 129. Thus, when a healthcare provider engages the ratchet 191 and moves the ratchet 191 downwardly out of engagement with the pawl 129 gravity will keep the teeth 192 from being engaged with the pawl 129. This will assist in reducing noise when the speculum 100 is pivoted open. The healthcare provider need only move their thumb from the toggle 187 to the ratchet 191 to adjust the speculum 100 vertically and allow the upper bill assembly 101 to pivot relative to the bottom bill assembly 102.

Figure 14:
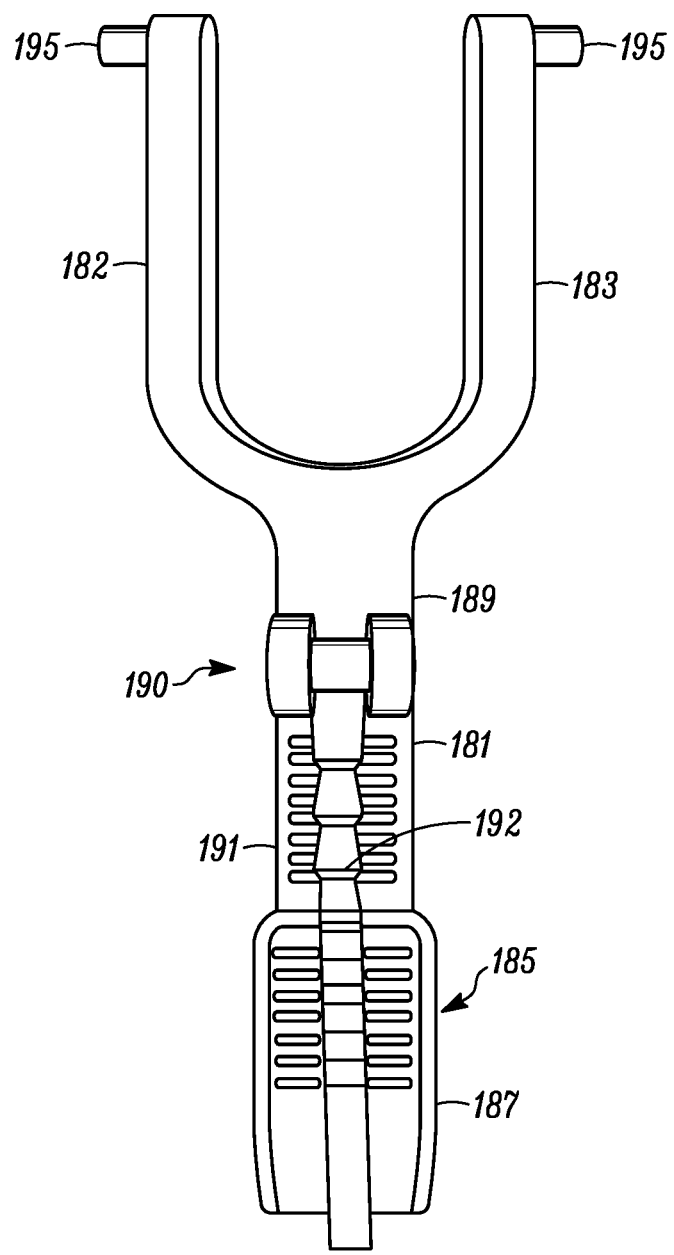
FIG. 14 is a rear view of a yoke according to an example embodiment.
Figure 15:
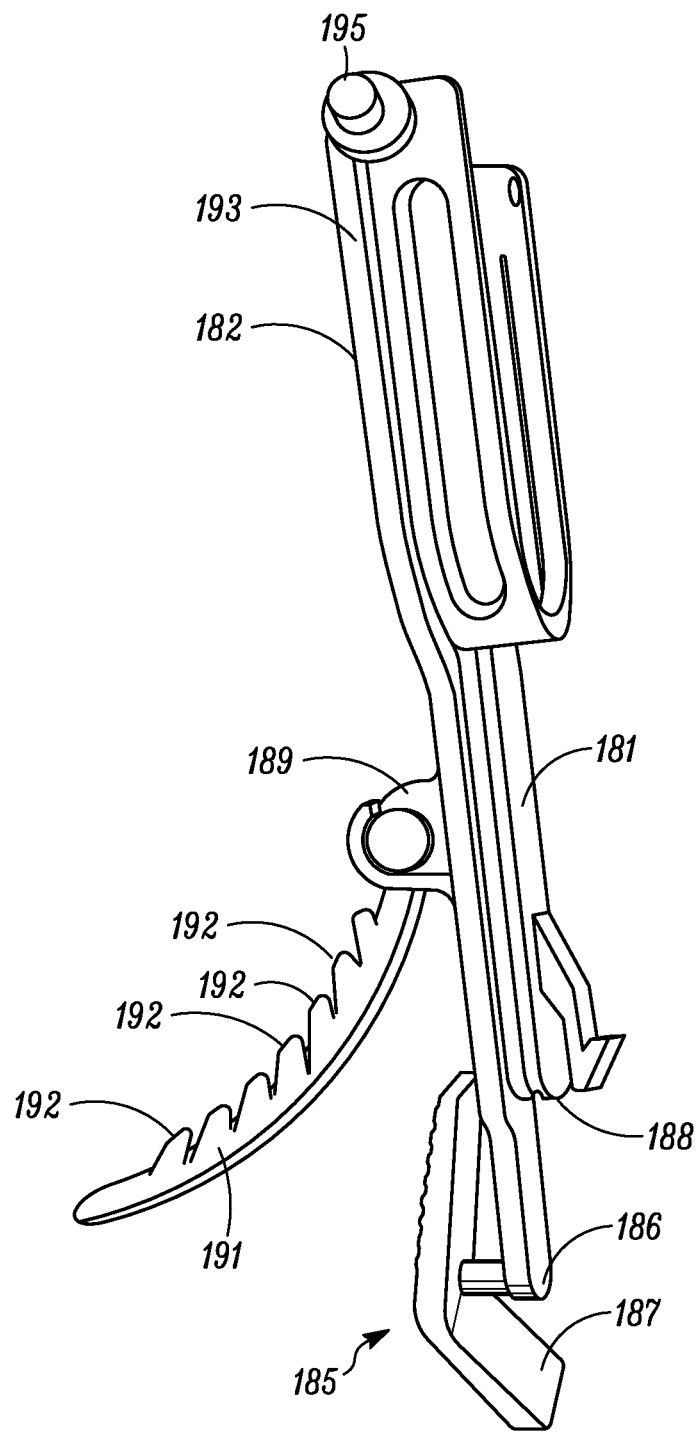
FIG. 15 is a side view of the yoke.
Figure 16:
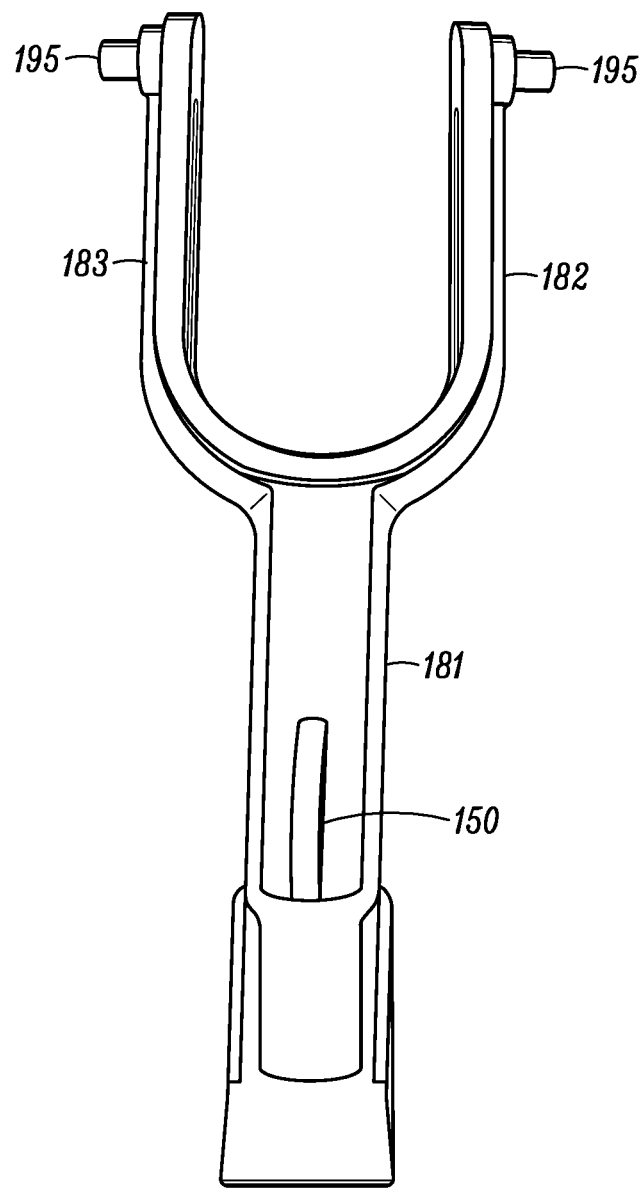
FIG. 16 is a front view of the yoke.

The teeth 192 have an engagement surface that faces the back toward the base 181 and grip 133, in use. In FIG. 14, the ratchet 191 is fully rotated downwardly along the base 181 with the teeth shown outwardly of the page. This is not the use position. The latch surface extends at an acute angle relative to the elongate body of the ratchet 191. The teeth 192 further have a rounded rear surface or angled rear surface that will allow the pawl to ratchet forward, if the teeth are engaged with the pawl. The latch surface will not allow the pawl to slip proximally toward the health care provider. Thus, the teeth 192, when engaged with the pawl 129 will not release away from the patient (proximally toward the health care provider) without action by the healthcare provider. The proximal movement of the pawl and handle of the engagement structure 128 opens the bills. The latch surface of the teeth prevents closing of bills. In order to close the bills 121, 131, the healthcare provider releases the ratchet 191 downwardly and the upper bill 121 is freely movable.

While the above embodiments describe the teeth as extending upwardly from the elongate body of the ratchet 191, it is with the scope of the present invention to align the teeth 192 in directions other than upwardly. However, it is not desirable to have the teeth in a directly downward direction as this may increase the noise of the speculum or alter its operation. Downward direction can be toward the base of the handle 133 in an example. Downward can also be defined as the direction of the ratchet teeth shown in U.S. Patent Application Publication No. 2014/0148653. The ratchet teeth of the present disclosure do not extend in the direction as shown in the Publication No. 2014/0148653. In an example, the ratchet 191 is mounted askew from the elongate direction of the grip 133. In an example, the ratchet 191 is mounted about 5 to 20 degrees offset from the elongate direction of the grip 133 or base 181. In an example, the ratchet 191 can be mounted rotated up to about 90 degrees relative to the longitudinal direction of the grip 133 or the base 181. In other examples, the ratchet can be mounted 15-45 degrees relative to the longitudinal direction of the grip 133 or the base 181.

Figure 17:
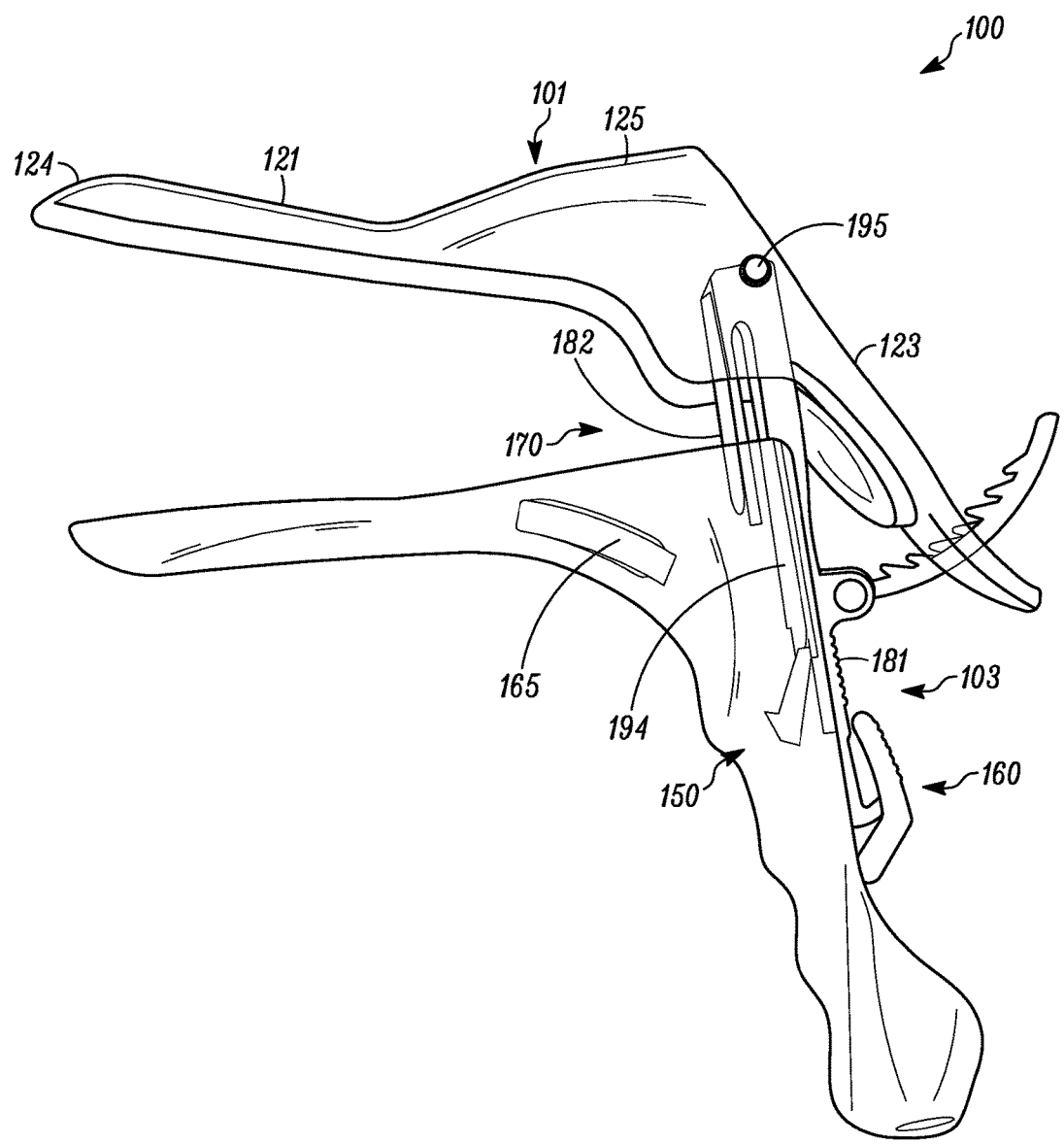
FIG. 17 is an elevational view of a speculum according to an example embodiment.

The yoke arms 182, 183 each include an elongate recess 193 that is adapted to receive the elongate protrusions 194 that form the guide 171. See FIGS. 15 and 17. The elongate protrusions 194 extend vertically in the proximal end 125 of the lower bill assembly 102. See FIGS. 10, 12-13 and 17. The mating of the elongate protrusions 194 in the recesses 193 allows the free vertical movement of the upper bill assembly 101 relative to the lower bill assembly 102.

A pivot pin 195 is positioned at the top, free end of each of the arms 182, 183. The pivot pins 195 extend into the cylindrical apertures 122 at the rear of the upper bill assembly 101. The pivot pins 195 are horizontally aligned to define the pivot axis about which the upper bill assembly 101 pivots relative to the lower bill assembly 102. The pivot connection 189 for the pivoting the bills and the pivot pins 195 are fixed in place relative to each other on the yoke 103. A healthcare provider to pivot the upper bill assembly 101 to further separate the upper bill 121 from the lower bill 131 by disengaging the ratchet 191 from the pawl 129 and pressing or releasing the engagement structure 128.

A locking mechanism, which is formed by the ratchet 191 and pawl 129, selectively allows the upper bill assembly 101 to pivot at the pivots 195 when the ratchet 191 is free of the pawl 129. The latch may be present in order to lock the relative position of the upper bill assembly 101 and lower bill assembly 102, and specifically, the bills 121, 131, 4 to one another or to otherwise limit the orientation of the bill assemblies 101, 102 and bills 121, 131 to one another.

The presently described speculum 100 is closed with the bills 121, 131 on top of each other with the sides and distal ends 124, 134 aligned for insertion. Once inserted and properly oriented in the patient, the healthcare provider may engage the toggle 187 to release the latch to allow vertical movement of the upper bill assembly 101 relative to the lower bill assembly 102. Once the toggle 187 is released the assemblies 101, 102 are fixed against vertical movement. If the healthcare provider needs further viewing then the ratchet 191 is engaged and released from the pawl 129 for free movement. The engagement surface 128 is held by the healthcare provider and pivoted at the pivot pins 195 to either open or close the bills 121, 131 about the pivot axis defined by the pivot pins 195. This pivoting the bills 121, 131 allows the medical care provider to open a body cavity or canal, e.g., the vagina, and have an improved site into the body cavity. When operating the speculum, the presently disclosed device may operate with reduced noise compared to prior speculum. The teeth of the ratchet being completely removed from contact with the pawl or handle during spreading of the bills about the pivot reduces noise, e.g., a ratcheting sound. The ratchet is positioned to be released when the user's thumb engages the lever end of the bill, e.g., the engagement structure. To relatch the bills against pivoting to a closed position, the user moves the ratchet upwardly and can simultaneously hold the engagement structure with the same thumb. There is no need to use the other hand, thus, the present device 100 can be used with a single hand. Likewise the same thumb that is used to pivot the bills can also be used to engage the vertical latch mechanism to release the bills, vertical adjust the bills relative to each other and allow the bills to be fixed in the new vertical position.

The speculum 100 may be manufactured in a rigid material, e.g., a metal or a polymer, or a combination thereof. In the case of a polymer construction, the latch mechanism being formed as described herein to reduce the noise produced when operating the speculum. The polymer latch mechanism can be designed to not make the clinking noise of a metal on metal latch.

The present speculum 100 includes a first release structure that allows the bill assemblies to move vertically relative to each other to separate the bills. A second release structure allows the bills to pivot at a pivot axis that is outside the patient's body to further separate the bills to further open an orifice of the patient's body. In an example, the second release structure allows for the adjustment, e.g., further opening of the orifice after the speculum is inserted. The first release structure can include the latch mechanism 160. The second release structure can include the locking mechanism, e.g., the ratchet 191 and pawl 129. Both the first release structure and the second release structure can be operated using a single digit, e.g., a thumb. The speculum 100 can be operated using a single hand, leaving the other hand free for other uses.

The light source 105 is described herein as within the speculum 100. This can be during use. The light source 105 may be removable for recharging or before disposal of the speculum 100. In some examples, the speculum 100 is a single use device that is used and then discarded. The light source 105 can also be a wired light source that receives electrical power or light from a device that is outside the speculum.

The presently described speculum can be used for gynecological examination or a gynecological surgical procedure. The speculum can be operated with a single hand of the medical professional to pivot, horizontally widen or operate the light. The speculum can be inserted into a patient's vagina to separate the vaginal walls, thus allowing the internal genital organs to be examined. The speculum is non-metal with few exposed joints, sharp edges, and cold metal, which are universally disliked by patients. The hinged joints and bill edges of the speculum are designed to minimize the risk of pinching, scraping, or otherwise traumatize the supporting tissues in the area being examined, while providing the medical professional with a controllable speculum with a pivoting mechanism that does not clink like metal and can be self-locking in place, while being easily released by the hand of the medical provider. The ratchet is positioned centrally along the base of the handle to be easily engaged be either the right or left thumb of the medical professional.

The embodiments of the present disclosure may be directed to a reduced noise or reduced "clicking" speculum. The speculum may solve a long-standing problem related to patient comfort. The speculum may remove the "racheting" sound from a medical procedure thereby making the patient more relaxed. A more relaxed patient means the procedure goes more smoothly.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A vaginal speculum comprising:
   an upper bill;
   a lower bill downwardly of the upper bill;
   a yoke moveably joining the upper bill to the lower bill; and
   a ratchet to hold the upper bill and lower bill at a position relative to each other, the ratchet including teeth facing upwardly to selectively hold the upper bill and lower bill, wherein the upper bill includes an aperture through which the ratchet extends and a pawl that defines an upper edge of the aperture, and wherein the ratchet is pivotally connected to the yoke to allow the ratchet to move vertically upwardly into engagement with the pawl and move downwardly out of engagement with the pawl.

2. The vaginal speculum of claim 1, wherein the yoke includes a pivot about which the upper bill pivots.

3. The vaginal speculum of claim 2, wherein the yoke allows vertical movement of the upper bill relative to the lower bill.

4. The vaginal speculum of claim 3, wherein the yoke includes a toggle to hold the yoke relative to the lower bill.

5. The vaginal speculum of claim 1, wherein the yoke includes a pivot axis at a top thereof at which the upper bill pivots on the yoke.

6. The vaginal speculum of claim 1, wherein the lower bill includes a first latch and the yoke includes a second latch that engages the first latch to prevent the yoke from being released from the lower bill.

7. The vaginal speculum of claim 1, wherein the yoke includes arms above a base with the arms engaging an upper part of the lower bill to guide the yoke relative to the lower bill.

8. The vaginal speculum of claim 7, wherein the yoke includes a recess in each of the arms and a guide on both sides of the lower bill to engage in the recesses.

9. The vaginal speculum of claim 1, wherein the yoke includes a pivot about which the upper bill pivots;
   wherein the yoke allows vertical movement of the upper bill assembly relative to the lower bill;
   wherein the yoke includes a toggle to hold the yoke relative to the lower bill; and
   wherein the yoke includes a pivot axis at a top thereof at which the upper bill pivots on the yoke.

10. A vaginal speculum comprising:
    an upper bill assembly;
    a lower bill assembly;
    a yoke moveably joining the upper bill assembly to the lower bill assembly to allow the upper bill assembly to pivot and to allow the upper bill assembly and the lower bill assembly to move vertically relative to each other; and
    a ratchet means for releasing the upper bill assembly and the lower bill assembly for relative movement such that teeth are completely free for movement in a first position and moveable to engaged position for holding the upper bill assembly from pivoting relative to the lower bill assembly, wherein the upper bill assembly includes an aperture through which the ratchet means extends, and wherein the ratchet means includes a pawl that defines an upper edge of the aperture, and wherein the ratchet means is pivotally connected to the yoke to allow the ratchet means move vertically upwardly into engagement with the pawl and move downwardly out of engagement with the pawl.

11. The vaginal speculum of claim 10, wherein the yoke includes a pivot about which the upper bill assembly pivots;
    wherein the yoke includes a toggle to hold the yoke relative to the lower bill assembly; and
    wherein the yoke includes a pivot axis at a top thereof at which the upper bill assembly pivots on the yoke.

12. The vaginal speculum of claim 11, wherein the yoke includes a pivot about which the upper bill assembly pivots, the ratchet means being adapted to reduce noise when pivoting the upper bill assembly relative to the lower bill assembly.

13. The vaginal speculum of claim 10, wherein the yoke includes a toggle to hold the yoke relative to the lower bill assembly.

14. The vaginal speculum of claim 10, wherein the yoke includes a pivot axis at a top thereof at which the upper bill assembly pivots on the yoke.

15. A vaginal speculum comprising:
    an upper bill;
    a lower bill downwardly of the upper bill;
    a yoke moveably joining the upper bill to the lower bill; and
    a ratchet to hold the upper bill and lower bill at a position relative to each other, the ratchet including teeth facing upwardly to selectively hold the upper bill and lower bill, wherein the lower bill includes a first latch and the yoke includes a second latch that engages the first latch to prevent the yoke from being released from the lower bill.

* * * * *

UNITED STATES PATENT AND TRADEMARK OFFICE
CERTIFICATE OF CORRECTION

PATENT NO. : 10,492,673 B2
APPLICATION NO. : 15/612656
DATED : December 3, 2019
INVENTOR(S) : Corey Wallace and Kelley Kuehne Page 1 of 1

It is certified that error appears in the above-identified patent and that said Letters Patent is hereby corrected as shown below:

In the Claims
Column 10, Line 4, In Claim 9, after "bill" delete "assembly".

Signed and Sealed this
Fifteenth Day of September, 2020

Andrei Iancu
*Director of the United States Patent and Trademark Office*